United States Patent

Rasmusson et al.

Patent Number: 5,091,380
Date of Patent: Feb. 25, 1992

[54] N-MONOSUBSTITUTED ADAMANTYL/NORBORNANYL 17β-CARBAMIDES OF 3-CARBOXY-ANDROST-3,5-DIENES AS TESTOSTERONE 5α-REDUCTASE INHIBITORS

[75] Inventors: Gary H. Rasmusson, Watchung; Richard L. Tolman, Warren; Gool F. Patel, Millington, all of N.J.

[73] Assignee: Merck & Co., Inc., Rahway, N.J.

[21] Appl. No.: 545,264

[22] Filed: Jun. 28, 1990

[51] Int. Cl.$^5$ .......................... A61K 31/56; C07J 53/00
[52] U.S. Cl. .................................... 514/169; 552/610
[58] Field of Search ....................... 552/610; 514/169

[56] References Cited

U.S. PATENT DOCUMENTS

| | | | |
|---|---|---|---|
| 2,227,876 | 1/1941 | Bolt | 546/77 |
| 3,239,417 | 3/1966 | Tullin et al. | 546/77 |
| 3,264,301 | 8/1966 | Doorenbos et al. | 546/77 |
| 3,285,918 | 11/1966 | Doorenbos et al. | 546/77 |
| 4,220,775 | 9/1980 | Rasmusson et al. | 546/77 |
| 4,317,817 | 3/1982 | Blohm et al. | 424/226 |
| 4,377,584 | 3/1983 | Rasmusson et al. | 546/77 |
| 4,732,897 | 3/1988 | Caineli et al. | 514/222 |
| 4,760,071 | 1/1988 | Rasmusson et al. | 514/284 |
| 4,845,104 | 7/1989 | Carlin et al. | 514/284 |
| 4,859,681 | 8/1989 | Rasmusson et al. | 514/284 |
| 4,882,319 | 11/1989 | Holt et al. | 514/119 |
| 4,910,226 | 3/1990 | Holt et al. | 514/593 |

FOREIGN PATENT DOCUMENTS

| | | |
|---|---|---|
| 970692 | 7/1975 | Canada |
| 0314199 | 3/1980 | European Pat. Off. |
| 155096 | 9/1985 | European Pat. Off. |
| 0289327 | 2/1988 | European Pat. Off. |
| 0277002 | 6/1988 | European Pat. Off. |
| 0004949 | 10/1989 | European Pat. Off. |
| 0343954 | 11/1989 | European Pat. Off. |
| 0375344 | 6/1990 | European Pat. Off. |
| 0375345 | 6/1990 | European Pat. Off. |
| 0375347 | 6/1990 | European Pat. Off. |
| 0375349 | 6/1990 | European Pat. Off. |

OTHER PUBLICATIONS

Endo., vol. 91, No. 2 (1972) by Neri et al.
Steroids, 14, 269 (1969), by Nayfeh et al.
Endo., vol. 92, p. 1216 (1973) by Voigt and Hsia.
J. Pharm. Sci., 62, 4, pp. 638–640 (1973) by Doorenbos and Solomons.
J. Pharm. Sci., 60, 8, pp. 1234–1235 (1971), by Doorenbos and Brown.
J. Pharm., 63, 4, pp. 620–622 (1974) by Doorenbos and Kim.
J. Med. Chem. (1986) 29 (11): pp. 2298–3115 by Rasmusson et al.
Prostate (1986) 9 (1): pp. 65–75 by Brooks et al.
Steroids (1986) 47 (1)*, pp. 1–19 by Brooks et al.
Endocr. (1985) 117 (2): pp. 571–579, by Liang et al.
J. Med. Chem. (1984) 27 (12)*, pp. 1690–1701, by Rasmusson et al.
J. Org. Chem. (1981) vol. 46, No. 7, pp. 1442–1446.
Chem. Abstracts, vol. 95, 109055j, by T. Liang et al.
JNCI, vol. 74, No. 2, pp. 475–481 (Feb. 1985).
The Prostate, vol. 10, pp. 189–197 (1987) by G. L. Andriole et al.
J. Endocr., vol. 57, pp. 111–121 (1973), by K. D. Bingham et al.
Toxicol. Appl. Pharmacol., vol. 103, pp. 222–227 (1990), by G. L. Kedderis et al.
Bioinorganic Chemistry, 17, pp. 372–376 (1986) by B. W. Metcalf et al.
Biochemistry, 1990, vol. 29, pp. 2815–2824, by M. A. Levy et al.
J. Med. Chem., 1990, vol. 33, pp. 943–950, D. A. Holt et al.
J. Steroid Biochem., vol. 34, Nos. 1–6, pp. 571–575 (1989), by M. A. Levy et al.
J. Med. Chem., vol. 33, pp. 937–942 (1990) by D. A. Holt et al.
TIPS, Dec. 1989, vol. 10, pp. 491–495, by D. W. Metcalf et al.
Steroids, vol. 35, No. 3 (Mar. 1980), pp. 1–7.
Prostate, vol. 9, pp. 311–318.(1986) by N. Stone et al.
Steroids, vol. 47, No. 1, pp. 1–19 (1986) by J. R. Brooks et al.
Lancet, Nov. 1986, No. 8515, pp. 1095–1096.
J. Clin. Endocrin. and Metab., vol. 55, No. 1, pp. 188–193 (1987).

Primary Examiner—Mukund J. Shah
Assistant Examiner—Jyothsna Venkat
Attorney, Agent, or Firm—Salvatore C. Mitri; Charles M. Caruso

[57] ABSTRACT

N-monosubstituted adamantyl/norbornanyl 17β-carbamides of 3-carboxy-androst-3,5-dienes as testosterone 5α-reductase inhibitors of the formula:

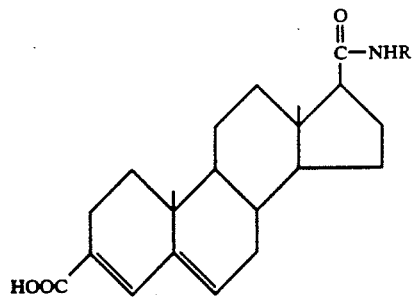

wherein R is a hydrocarbon radical selected from substituted or unsubstituted 1- or 2-adamantyl or 1-, 2- or 7-norbornanyl and pharmaceutically acceptable salts or esters thereof. Also described is a pharmaceutical formulation. The above compounds are active as testosterone 5α-reductase inhibitors and thus are useful topically for treatment of acne, seborrhea, female hirsutism, and systemically in treatment of benign prostatic hypertrophy.

5 Claims, No Drawings

N-MONOSUBSTITUTED ADAMANTYL/NORBORNANYL 17β-CARBAMIDES OF 3-CARBOXY-ANDROST-3,5-DIENES AS TESTOSTERONE 5α-REDUCTASE INHIBITORS

BACKGROUND OF THE INVENTION

The present invention is concerned with novel 17β-N-monosubstituted adamantyl or norbornanyl 3-carboxy-androst-3,5-dienes compounds and the use of such compounds as testosterone 5α-reductase inhibitors.

DESCRIPTION OF THE PRIOR ART

It is known in the art that certain undesirable physiological manifestations, such as acne vulgaris, seborrhea, female hirsutism, and male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal anti-androgens having undesirable hormonal activities of their own. The estrogens, for example, not only counteract the effect of the androgens but have a feminizing effect as well. Non-steroidal anti-androgens have also been developed, for example, 4'-nitro-3'-trifluoromethylisobutyranilide. See Neri et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone 5α-reductase. It therefore has been postulated and demonstrated that inhibitors of testosterone 5α-reductase will serve to prevent or lessen symptoms of hyperandrogenic stimulation. Nayfeh et al., Steroids, 14, 269 (1969) demonstrated in vitro that methyl 4-androsten-3-one-17β-carboxylate was a testosterone 5α-reductase inhibitor. Then Voigt and Hsia, Endocrinology, 92, 1216 (1973), Canadian Pat. No. 970,692, demonstrated that the above ester and the parent free acid, 4-androsten-3-one-17β-carboxylic acid are both active inhibitors of testosterone 5α-reductase in vitro. They further demonstrated that topical application of either testosterone or 5α-dihydrotesterone caused enlargement of the female hamster flank organ, an androgen dependent sebaceous structure. However, concomitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone 5α-reductase.

A number of androstene 5α-reductase inhibitors are known in the art. For example:

(1) *Bioinorganic Chemistry*, 17, pp. 372–376 (1986), by B. W. Metcalf, et al, describes the inhibition of human steroid 5α-reductase (EC 1.3.1.30) by 3-androstene-3-carboxylic acids;

(2) *Biochemistry* (1990) Vol. 29, pp. 2815–2824, by M. A. Levy, et al, describes the mechanism of enzyme-inhibitor interaction in the inhibition of rat liver steroid 5α-reductase by 3-androstene-3-carboxylic acids;

(3) *J. Med. Chem.* (1990) Vol. 33, pp. 943–950 (1990), by D. A. Holt, et al, describes the inhibition of steroid 5-α reductase by unsaturated 3-carboxysteroids;

(4) *J. Steroid Biochem.*, Vol. 34, Nos. 1–6, pp. 571–575 (1989), by M. A. Levy, et al, describes the interaction mechanism between rat prostatic steroid 5-alpha reductase and 3-carboxy-17-β substituted steroids;

(5) *J. Med. Chem.* (1990) Vol. 33, pp. 937–942, by D. A. Holt, et al, describes the new steroid class of A ring aryl carboxylic acids; (6) *TIPS* (December 1989) Vol. 10, pp. 491–495, by D. W. Metcalf, et al, describes the effect of inhibitors of steroid 5α-reductase in benign prostatic hyperplasia, male pattern baldness and acne; and (7) *EPO Publn. No.* 0 289 327, to D. A. Holt, et al, (SmithKline Beckmann) describes steroidal 3-carboxylic acid derivatives as useful 5-α reductase inhibitors.

However, none of the above references specifically suggest that any of the novel 3-carboxyandrost-3,5-diene-17-beta-N-monosubstituted adamantyl/norbornanyl compounds of the present invention would have utility as potent testosterone 5α-reductase inhibitors.

SUMMARY OF THE INVENTION

The present invention relates to novel N-(monosubstituted) adamantyl and norbornanyl 17β-carbamides of 3-carboxy-androsten-3,5-diene compounds, processes for their preparation, pharmaceutical formulations comprising these novel compounds as active ingredients and methods of inhibiting testosterone 5α-reductase and of treating hyperandrogenic conditions with the novel compounds and their pharmaceutical formulations.

In accordance with this invention, there is provided a compound of the formula:

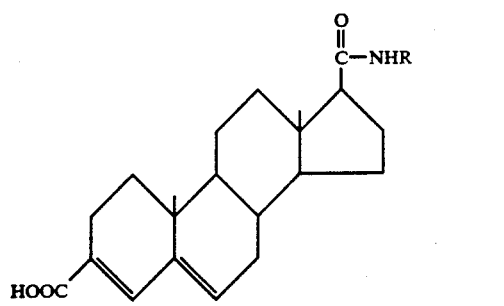

wherein R is a hydrocarbon radical selected from substituted or unsubstituted 1- or 2-adamantyl or 1- or 2-norbornanyl, and pharmaceutically acceptable salts or esters thereof.

BRIEF DESCRIPTION OF THE INVENTION AND PREFERRED EMBODIMENTS

Representative compounds of the present invention include the following:

17β-(N-1-adamantylcarbamoyl)-3-carboxy-androst-3,5-diene;

17β-(N-2-adamantylcarbamoyl)-3-carboxy-androst-3,5-diene;

17β-(N-1-norbornanylcarbamoyl)-3-carboxy-androst-3,5-diene;

17β-(N-2-norbornanylcarbamoyl)-3-carboxy-androst-3,5-diene; and pharmaceutically acceptable salts or esters thereof.

The 1-, 2-adamantyl or 1-, 2- or 7-norbornanyl moieties can be substituted with one or more substituents of the following: $C_1$-$C_4$ linear/branched alkyl, including methyl, ethyl, isopropyl, n-butyl; nitro; oxo; $C_7$-$C_9$ aralkyl, including benzyl; $(CH_2)n$ $COOR^2$ where n is 0-2 and $R^1$ is H or $C_1$-$C_4$ linear/branched alkyl including methyl, ethyl; $CH_2OH$; OH; $OR^2$ where $R^2$ is $C_1$-$C_4$ linear/branched alkyl including methyl, ethyl; halo, including fluoro, bromo, iodo; COOH; $COOR^2$, where $R^1$ is linear/branched $C_1$-$C_4$ alkyl; —$CONH_2$; $CH_2NH_2$; $CH_2NHCOR^3$ where $R^3$ is $C_1$-$C_4$ linear/branched alkyl including methyl, ethyl; phenyl; o, m, p-substituted phenyl including p-nitro, p-amino and p-sulfo; or cyano.

Also included within the scope of this invention are pharmaceutically acceptable salts or esters, where a basic or acidic group is present on the adamantyl or norbornanyl moiety. When an acidic substituent is present, i.e. —COOH, there can be formed the ammonium, sodium, potassium, calcium salt, and the like, for use as the dosage form.

Where a basic substitutent group is present, i.e. amino, acidic salts, i.e. hydrochloride, hydrobromide, acetate, pamoate, and the like, can be used as the dosage form.

Also, in the case of the —COOH or —OH group being present, pharmaceutically acceptable esters can be employed, e.g. acetate, maleate, pivaloyloxymethyl and the like, and those esters known in the art for modifying solubility or hydrolysis characteristics for use as sustained release or prodrug formulations.

Representative examples include the following (where AD is adamantyl): 3,5,7-trinitro-1-AD; 4-oxo-1-AD; 1-benzyl-1-AD; 4,4-dimethyl-1-Ad; 3,7-dimethyl-5-carboxymethyl-1-AD; 3-carboxymethyl-1-AD; 3-chloro-1-AD; 1,3-dihydroxy-6,6-dimethyl-2-AD; 3-chloro-1-AD; 4-carbethoxy-2-AD; 4-carboxy-2-AD; 3-isopropyl-1-AD; 3-n-butyl-1-AD; 3-propyl-1-AD; 3-,5-diethyl-1-AD; 3-hydroxymethyl-1-AD; 2-carboxy-1-AD; 3-methyl-1-AD; 5-hydroxy-2-AD; 2-hydroxy-1-AD; 1-aminomethyl-1-hydroxy-2-AD; 2-oxo-1-AD; 2-phenyl-2-AD; 1-amino-methyl-2-AD; 1-carboxy-2-AD; 1-aminocarbonyl-2-AD; 3-hydroxy-5,7-dimethyl-1-AD; 4-fluoro-1-AD; 3-fluoro-1-AD; 4-hydroxy-2-AD; 3-phenyl-1-AD; 3-(p-aminophenyl)-1-AD; 3-(p-nitrophenyl)-1-AD; 3-methyl-5-hydroxymethyl-1-AD; 3,5-dimethyl-4-hydroxy-1-AD; 2-hydroxymethyl-2-AD; 3-(p-sulfophenyl)-1-AD; 3-methyl-5-ethyl-1-AD; 2-carboxy-2-AD; 3,5-7-trimethyl-1-AD; 4-iodo-2-AD; 4-bromo-2-AD; 4-chloro-2-AD; 1-acetylaminomethyl-2-AD; 1-carboxymethyl-2-AD; 1-methyl-2-AD; 1-aminocarboxylmethyl-2-AD; 1-aminocarboxyl-1-AD; 2-cyano-2-AD; 3,5-dimethyl-7-ethyl-1-AD; 4-hydroxy-1-AD; 1-hydroxy-2-AD; 5-carboxy-3-methyl-1-AD; 3,5-dimethyl-7-carboxy-1-AD; 3-carboxy-1-AD; 3-hydroxy-1-AD; and the like.

Representative examples include the following (where NB is norbornanyl): 2-NB; 1,7,7-trimethyl-4-phenyl-2-NB; 3-carboxy-2-NB; 3-phenyl-2-carboxy-2-NB; 2-cyano-3-phenyl-2-NB; 3-hydroxy-4,7,7-trimethyl-2-NB; 6-hydroxymethyl-2-NB; 5-cyano-2-NB; 3-allyl-2-NB; 1-NB; 7,7-dimethyl-1-hydroxymethyl-2-NB; 3-methoxy-4,7,7-trimethyl-2-NB; 3-aminocarbonyl-2-NB; 3-ethoxycarbonyl-2-NB; 3,3-dimethyl-2-NB; 7-oxo-1-NB; 3-phenyl-2-NB; 1-carboxymethyl-7,7-dimethyl-2-NB; 1-ethyl-2-NB; 1-methyl-2-NB; 2,2,3,3,5,5,6,6,7,7-decafluoro-1-NB; 3-hydroxy-2-NB; 3-chloro-2-NB; 3-(p-methoxyphenyl)-2-NB; 2,2-dimethyl-3-methylene-7-NB; 3-oxo-2-NB; 1-methoxy-2-NB; 7-NB; 3-isopropyl-2-NB; 2-bromo-1-NB; 3-chloro-1-NB; and the like.

Procedures for preparing the adamantyl and norbornanyl amines included within the scope of this invention, including the representative examples above, are well known in the art.

The novel compounds of formula I of the present invention can be prepared by methods starting with the known steroid acid (II) of the formula:

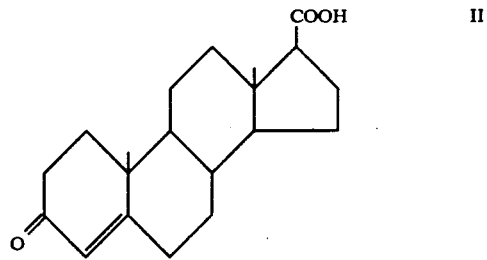

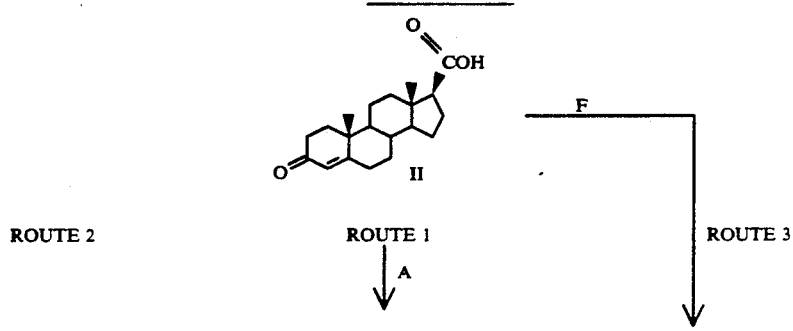

FLOWSHEET

ROUTE 2        ROUTE 1        ROUTE 3

-continued
FLOWSHEET

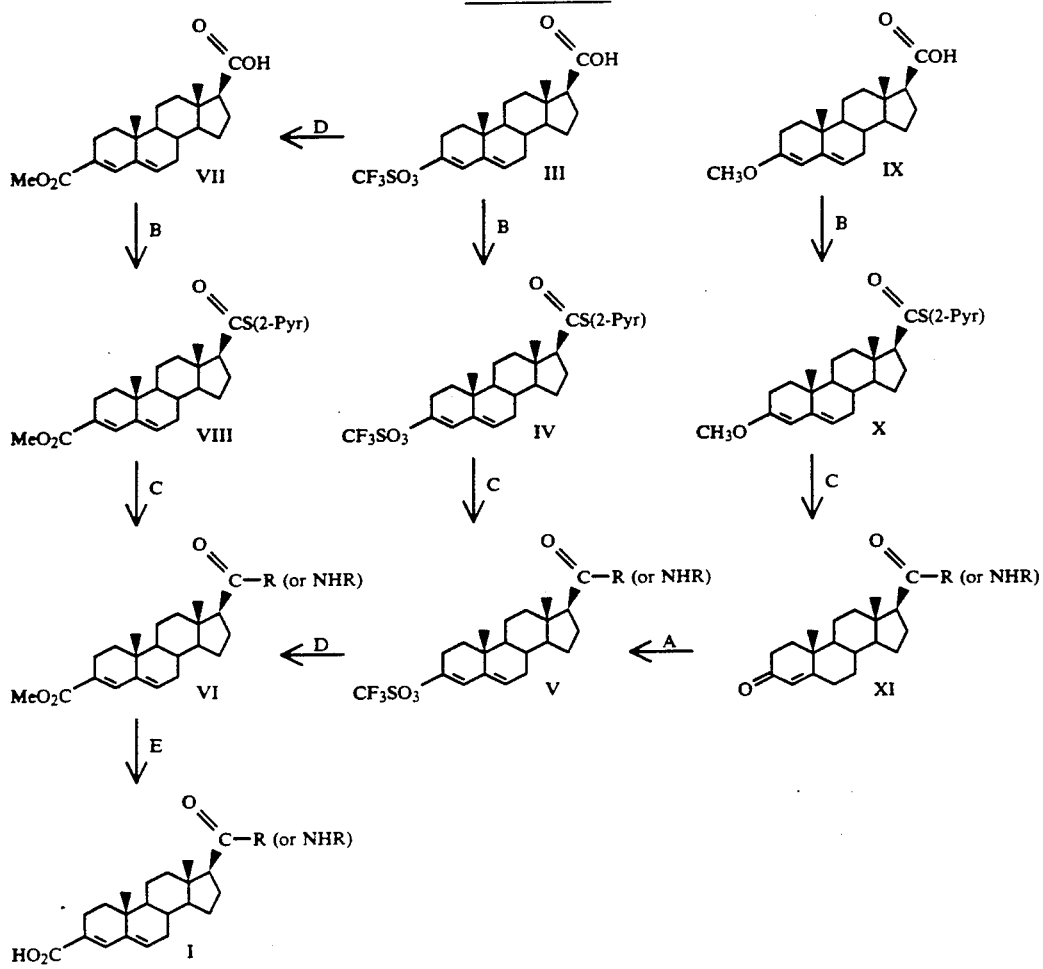

Referring to the above flowsheet, three routes are described to produce the novel compound I of this invention.

The common features of the routes are that, unlike the prior art, (1) they involve creating the 17-carbamoyl substitutent by a displacement reaction involving an activated ester, e.g. 2-thiopyridyl, and (2) they involve 3-carbonylation of a 17-carbonyl-containing steroid. Common steps are employed in the three procedures, e.g. amine-ester condensation, which are designated by a letter, i.e. Step C, for ease in following the flow chart.

Referring to Route 1, the 3-acyl acid II is converted to the 3-trifluoromethylsulfonyloxy derivative III (Step A) by treating II with trifluoromethylsulfonyl anhydride and a tertiary amine, e.g. lutidine, in e.g. methylenechloride at e.g. room temperature (RT) under dry and anhydrous conditions for e.g. 1–4 hours. Isolation and purification of the product is conventional.

The activated ester IV is produced (Step B) by treating III with 2,2-dithiopyridyl (Aldrithiol) and triphenylphosphine in, e.g. THF, toluene at RT under anhydrous conditions for 8–24 hours. Isolation/purification is accomplished by conventional procedures.

The 17-carbamoyl derivative V is produced (Step C) by treating IV with an adamantyl amine or norbornanyl amine, described hereinabove, in THF or $CH_2Cl_2$ solvent, at room temperature for 1–16 hours. Isolation/purification is by conventional chromatography.

The 3-alkyl ester VI is produced (Step D) by treating V under carbonylation conditions by bubbling carbon monoxide gas through a solution of V in e.g. methanol, containing palladium acetate catalyst, triphenylphosphine, and a tertiary organic amine, e.g. triethylamine, at RT, under anhydrous conditions/$N_2$ for 1–16 hours followed by conventional workup.

The final product I is made (Step E) by treating VI with NaOH or KOH in an alcoholic solvent e.g. methanol, at RT to reflux, for 1–4 hours under air-free conditions. Workup is conventional.

Note that, if R also contains a protected hydroxy group, e.g. with dimethyl-t-butyl-silyl, this may be removed (Step G) by treating with tetrabutylammonium fluoride in e.g. tetrahydrofuran with a small amount of added acetic acid, at 0° C.-reflux for 1–4 hours, prior to carrying out Step E.

Route #2 involves converting the starting steroid acid II to the 3-trifluoromethylsulfonyl ester III by the above-described Step A; carbonylating II to VII by Step D; forming the activated 2-pyridylthioester VIII by Step B; forming the 17-carbamoyl compound VI by Step C; and hydrolyzing the 3-ester to the 3-acid final product I by Step E.

Route #3 involves first converting the starting steroid acid II to the 3-alkoxy derivative IX (Step F) by treating II with, e.g. an alkyl orthoformate, e.g. trimethylorthoformate and a strong sulfonic acid, e.g. 2,4- dinitrobenzenesulfonic acid, in methanol (or ethanol if using triethylorthoformate at e.g. RT, for 0.25-2 hours. Isolation/purification is accomplished by hydrolyzing with base and adding water.

The 3-alkoxy-17-activated ester X is formed from IX by Step B; the 17-carbamoyl derivative XI is formed from X by Step C followed by an acid hydrolysis in the course of the workup by treating the obtained initial product with an acid, e.g. HCl, in MeOH, and stirring overnight at RT; the 3-trifluoromethylsulfonyl ester V is formed from XI by Step A; the 3-alkoxy carbonyl ester VI is formed from V under the carbonylation conditions of Step D; and product I is formed from VI by Step E.

The compounds of the present invention, prepared in accordance with the method described above, are, as already described, potent antiandrogens by virtue of their ability to specifically inhibit testosterone-5α-reductase.

Also included within this invention is a compound of the formula:

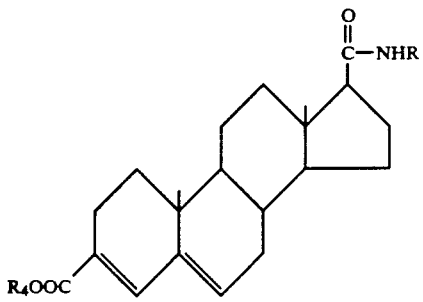

wherein R is a hydrocarbon radical selected from substituted or unsubstituted 1-, 2- or 7-adamantyl, 1- or 2-norbornanyl, $R^4$ is $C_1-C_4$ linear/branched alkyl, or trifluoromethylsulfonyloxy, and pharmaceutically acceptable salts or esters thereof. These compounds are useful intermediates in the production of the titled compounds of this invention.

Further included in this invention is a compound of the formula:

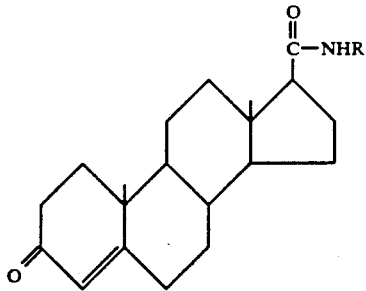

wherein R is a hydrocarbon radical selected from substituted or unsubstituted 1- or 2-adamantyl or 1- or 2-norbornanyl, and pharmaceutically acceptable salts or esters thereof, which are also useful intermediates for producing the title compounds of this invention.

Accordingly, the present invention is particularly concerned with providing a method of treating the hyperandrogenic conditions of acne vulgaris, seborrhea, and female hirsutism by topical administration, and a method of treating all of the above conditions as well as benign prostatic hypertrophy, by oral or parenteral administration, of the novel compounds of the present invention.

The present invention is thus also concerned with providing suitable topical, oral and parenteral pharmaceutical formulations for use in the novel methods of treatment of the present invention.

The compositions containing the compounds of the present invention as the active ingredient for use in the treatment of benign prostatic hypertrophy can be administered in a wide variety of therapeutic dosage forms in conventional vehicles for systemic administration, as, for example, by oral administration in the form of tablets, capsules, solutions, or suspensions, of by intravenous injection. The daily dosage of the products may be varied over a wide range varying from 50 to 2,000 mg. The compositions are preferably provided in the form of scored tablets containing 5, 10, 25, 50, 100, 150, 250, and 500 milligrams of the active ingredient for the symptomatic adjustment of the dosage to the patient to be treated. An effective amount of the drug is ordinarily supplied at a dosage level of from about 1 mg. to about 50 mg./kg. of body weight per day. Preferably the range is from about 1 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservative are employed when intravenous administration is desired.

For the treatment of acne vulgaris, seborrhea, female hirsutism, the compounds of the present invention are administered in the formula of pharmaceutical composition comprising the active compound in combination with a pharmacologically acceptable carrier adapted for topical administration. These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The method of preparing the novel 17β-N-monosubstituted adamantyl-carbamoyl compounds of the present invention, already described above in general terms, may be further illustrated by the following examples.

EXAMPLE 1

3-(Trifluoromethanesulfonyloxy)-3,5-androstadiene-17β-carboxylic acid

Step A (Route 1)

A solution of 3-oxo-4-androstene-17β-carboxylic acid (4.0 g., 12.5 mmoles), 2,6-di-tert-butyl-4-methyl pyridine (8.304 g., 31 mmoles) and trifluoromethane sulfonic anhydride (9.28 g., 33 mmoles) in 40 ml of methylene chloride was stirred at 22° C. for 2 hours and then was kept at 5° C. for 16 hours. The organic solvent was evaporated and the residue was dissolved in 200 ml of tetrahydrofuran containing 1.0 ml of water and 4.5 g. of 4-dimethylaminopyridine. This mixture was stirred at 22° C. for 20 hours and then acidified with 2N hydrochloric acid. The organic solvent was removed and the residue dissolved in methylene chloride, was applied to a column of 400 g. of silica gel. Elution with a 9:1 mixture of $CH_2Cl_2$: ethyl ether, containing 0.4% of formic acid (88%) afforded 6.2 g. of pure product. A portion triturated with acetonitrile gave an analytical sample, m.p. 140°-150° C. with decomposition.

Calcd.: C, 56.24; H, 6.07. Found: C, 56.71; H, 6.20.

EXAMPLE 2

S-(2-Pyridyl)-3-(trifluoromethanesulfonyloxy)-3,5-androstadiene-17β-thiocarboxylate Step B (Route 1)

A solution of the steroidal acid (6.2 g., 14.9 mmoles), triphenylphosphine (9.92 g., 38 mmoles) and 2,2'-dipyridyl disulfide (8.68 g., 39.5 mmoles) in 40 ml of toluene was stirred under nitrogen at 24° C. for 16 hours. The reaction mixture was eluted directly through 600 g. of silica gel with 3:1 cyclohexane:ethyl acetate. Fractions containing the desired product were combined and concentrated to leave 5.62 g. of the thiopyridyl ester as a glass. This material had appropriate nmr and mass spectra to confirm the structure and was used directly in the following Example.

EXAMPLE 3

17β-[4'-(tert-butyldimethylsiloxy)benzoyl]-3,5-androstadien-3-yl trifluoromethane sulfonate Step C (Route 1)

To a solution of the thiopyridyl ester of Example 2 (3.0 g., 5.5 mmole) in 30 ml of tetrahydrofuran at −50° C. was added slowly to 60 ml. of a Grignard reagent prepared from the reaction of 4-(tert-butyldimethylsiloxy)-phenyl bromide (11.2, 39 mmoles) with 2.44 grams of magnesium in 160 ml. of tetrahydrofuran. After stirring for one hour at −50° C., the mixture was warmed to 20° C. and diluted with 200 ml of a mixture of 1:1 methylene chloride and saturated aqueous ammonium chloride. The layers were well mixed and then separated. The organic layer was washed with saturated sodium chloride solution, then dried and evaporated to leave about 6 g. of residue. This residue was eluted through 380 g. of silica gel with 20:1 hexane/diethyl ether. Early fractions contained 1.21 g. of the bisadduct, 17β-(α,4,4'-trihydroxybenzhydryl)-3,5-androstadien-3-yl trifluoromethane sulfonate, identified by its mass and nmr spectra. Continued elution afforded 1.6 g. of the title compound the structure of which was confirmed by its nmr and mass spectra data.

EXAMPLE 4

Methyl 17β-[4'-tert-butyldimethylsiloxy)benzoyl]-3,5-androstadien-3-carboxylate

Step D (Route 1)

Into a solution prepared from 1.6 g. (2.5 mmoles) of the product of Example 3, triphenyl phosphine (84 mg., 0.32 mmole), palladium diacetate (32 mg., 0.14 mmole), triethylamine (0.96 ml., 0.7 g., 7 mmoles), 24 ml. of methanol and 24 ml. of dimethylformamide was bubbled carbon monoxide gas at 24° C. with vigorous stirring for 2 hours. The solution was then stirred for 16 hours under a carbon monoxide atmosphere. The solution was diluted with ethyl acetate, filtered and the filtrate washed well with water. After drying, the organic layer was evaporated to leave a noncrystalline residue which was chromatographed on silica gel eluted with 20:1 hexane/diethyl ether. The title compound (1.58 g.) was isolated as a noncrystalline material having the appropriate nmr and mass spectra to confirm the assigned structure.

EXAMPLE 5

Methyl 17β-(4-hydroxybenzoyl)-3,5-androstadien-3-yl carboxylate

Deblock Procedure G (Route 1)

A solution of the product of the previous Example 4 (1.58 g., 2.9 mmoles) in 32 ml. of tetrahydrofuran was cooled to 0° C. and was treated with 0.53 ml. of glacial acetic acid and 3.17 ml of a 1.0M solution of tetrabutyl ammonium fluoride in tetrahydrofuran. After stirring under nitrogen for one hour at 0° C., the solution was treated with 100 ml. each of ethyl acetate and saturated sodium bicarbonate solution. The separated aqueous layer was extracted with ethyl acetate. The combined organic layers were washed with water, saturated sodium chloride solution and then dried ($Na_2SO_4$) and evaporated. The residue (1.35 g.) was a noncrystalline solid with the appropriate nmr and mass spectra. A sample crystallized from acetonitrile had an m.p. of 208°-210° C.

Calcd: C, 77.39; H, 7.89. Found: C, 77.19; H, 7.73.

EXAMPLE 6

17β-(4-hydroxybenzoyl)-3,5-androstadien-3-yl carboxylic acid

Step E (Route 1)

A solution of 1.42 g. (3.27 mmoles) of the product of Example 5 in a mixture of 10 ml of 10% aqueous potassium hydroxide solution and 160 ml. of methanol was refluxed under nitrogen for 15 minutes. The cooled solution was diluted with 200 ml. of ethyl acetate and was treated with 200 ml. of water and sufficient concentrated hydrochloric acid to acidify the product. The aqueous layer was extracted with ethyl acetate and the combined ethyl acetate solutions were washed successively with water and saturated sodium chloride. The solution was dried ($Na_2SO_4$) and concentrated to leave 1.0 g. of a white solid. Recrystallization from methanol gave 700 mg of the title compound, m.p. 295° C. with decomposition: λ max; 268 nm (E=29,500).

Analysis Calcd. for $C_{27}H_{32}O_4 \cdot \frac{1}{2}H_2O$. C, 74.71; H, 7.77. Found: C, 74.55; H, 7.46.

EXAMPLE 7

3-methoxy-3,5-androstadiene-17β-carboxylic acid

Step F (Route 3)

A suspension of 7.0 g. (22 mmoles) of 3-oxo-4-androstene-17β-carboxylic acid in a mixture of 98 ml. of methanol and 20.3 ml. of trimethyl orthoformate was treated at 24° C. with 560 mg. of 2,4-dinitrobenzene sulfonic acid dihydrate. The reaction mixture became momentarily clear and then a precipitate formed. After stirring for 15 minutes, the reaction was neutralized with pyridine (about 1.7 ml). Water was added and the precipatated solid was removed by filtration, washed well with water and then dried to leave 7 g. of white solid (m.p. 203°-208° C.). Recrystallization from ethyl acetate gave 4.65 g. of pure title compound as analyzed by thin layer chromatography, and spectral data (nmr and mass spectra).

EXAMPLE 8

S-(2-pyridyl) 3-methoxy-3,5-androstadiene-17β-thiocarboxylate

Step B (Route 3)

A solution of 4.1 g. (12.4 mmoles) of the product of Example 7, 5.6 g. (25.5 mmoles) of 2,2'-dipyridyldisulfide and 6.72 g. (25.6 mmoles of triphenylphosphine in 30 ml. of toluene was stirred under nitrogen for 16 hours at 24° C. The reaction was concentrated to a thick gum which was eluted through 300 g. of silica gel with 9:1 cyclohexane/ethyl acetate. The desired thiopyridyl ester eluted after a bright yellow material and amounted to 3.2 g. of pure material as judged by its nmr spectrum and analysis by thin layer chromatography (4:1 cyclohexane/ethyl acetate, silica gel).

EXAMPLE 9

17β-benzoyl-4-androsten-3-one

Step C (Route 3)

To a solution of 2.95 g. (7.0 mmoles) of the thiopyridyl ester from Example 8 in 45 ml. of tetrahydrofuran was added dropwise at −78° C. under nitrogen 5.9 ml. of a 2.0M solution of phenyl magnesium chloride in tetrahydrofuran. After standing at −78° C. for one hour, the reaction was warmed to −30° C. and held for 20 minutes. The reaction was diluted with a mixture of methylene chloride and 10 ml. of 2N hydrochloric acid solution and then was warmed to room temperature with stirring. The phases were separated and the organic layer was washed successively with 1N sodium hydroxide solution, water and saturated sodium chloride solution. The residue obtained on evaporation was dissolved in 10% aqueous methanol containing 15 ml. of 2N hydrochloric acid. After stirring at 24° C. for 6 hours, the solution was concentrated and the residue dissolved in methylene chloride. This solution was washed with water, dried and evaporated. The residue crystallized from methylene chloride/ethyl acetate to give the title compound in two crops, total 1.45 g., m.p. 171°-173° C.

Anal. Calcd.: C, 82.93; H, 8.56. Found: C, 83.10; H, 8.76.

EXAMPLE 10

17β-benzoyl-3-trifluoromethanesulfonyloxy-3,5-androstadiene

Step A (Route 3)

To a solution of 1.3 g. (3.46 mmoles) of the diketosteroid from Example 9 and 9.92 mg. (4.83 mmoles) of 2,6-di-tert-butyl-4-methylpyridine in 15 ml. of methylene chloride was added at 0° C., 1.46 g. of trifluoromethane sulfonic anhydride. The reaction at 24° C. colored and darkened, and a precipitate formed. After 30 minutes, the reaction was diluted with methylene chloride and filtered. The filtrate was quickly washed successively with 5N hydrochloric acid, water, saturated sodium bicarbonate solution and saturated sodium chloride solution. The residue obtained on evaporation was chromatographed on 100 g. of silica gel with 9:1 cyclohexane/ethyl acetate to remove a faster moving impurity. Continued elution gave the title compound, 1.21 g., identified by its mass and nmr spectra. This material was used directly in the next Example.

EXAMPLE 11

Methyl 17β-benzoyl-3,5-androstadiene-3-carboxylate

Step D (Route 3)

The title compound was prepared in 75% yield from the product of Example 10 by a procedure analogus to that described in Example 4. The title compound, m.p. 121°-123° C., had nmr and mass spectra in accordance with the proposed structure.

EXAMPLE 12

17β-benzoyl-3,5-androstadiene-3-carboxylic acid

Step E (Route 3)

Saponification of the product of Example 11 gave, after recrystallization from acetonitrile, the title compound, m.p. 222°-225° C., λ max: 265 nm (ε=31,000), 246 nm (shoulder ε=28,300).

Anal. Calcd.: C, 80.16; H, 7.97. Found: C, 80.10; H, 7.99.

EXAMPLE 13

17β-Cyclohexylcarbonyl-4-androsten-3-one

Step C (Route 3)

The reaction of cyclohexyl magnesium chloride with the thiopyridyl ester (analogous to Example 9 and a workup similar to that described in Example 9) afforded the title compound, m.p. 159°-161° C.

Anal. Calcd.: C, 81.63: H, 10.01. Found: C, 81.36; H, 9.77.

EXAMPLE 14

17β-Cyclohexylcarbonyl-3-trifluoromethanesulfonyloxy-3,5-androstadiene

Step A (Route 3)

Treatment of the product of Example 13 by a procedure analogous to that of Example 10 afforded the title compound which was identified by its nmr and mass spectra.

EXAMPLE 15

Methyl 17β-cyclohexylcarbonyl-3,5-androstadiene-3-carboxylate

Step D (Route 3)

The title compound was prepared from the product of Example 13 by a procedure similar to that described in Example 4. The crude product was identified by its mass and nmr spectra and was used directly in the following Example.

EXAMPLE 16

17β-Cyclohexylcarbonyl-3,5-androstadiene-3-carboxylic acid

Step E (Route 3)

Saponification (analogous to the procedure of Example 12) of the product of Example 15 gave, after recrystallization from acetonitrile, the title compound, m.p. 217°-220° C. λ max: 266 nm (ε=27,100).

EXAMPLE 17

23-methyl-21-nor-4-cholene-3,20-dione

Step C (Route 3)

The reaction of iso-butyl magnesium chloride with the thiopyridyl ester (analogous to Example 9) and a workup similar to that described in Example 9 afforded the title compound m.p. 121°–123° C.

Anal. Calcd.: C, 80.85; H, 10.18. Found: C, 80.78; H, 10.38.

EXAMPLE 18

23-Methyl-3-trifluoromethanesulfonyloxy-21-nor-3,5-choladien-20-one

Step A (Route 3)

Treatment of the product of Example 17 according to a procedure similar to that of Example 10 afforded the title compound, pure by thin layer chromatography (silica gel, 4:1 cyclohexane/ethyl acetate) and identified by its nmr and mass spectra.

EXAMPLE 19

3-Carbomethoxy-23-methyl-21-nor-3,5-choladien-20-one

Step D (Route 3)

The title compound was prepared from the product of Example 18 by a procedure similar to that described in Example 4. The product, isolated by preparative thin layer chromatography, was identified by its nmr and mass spectra and was used directly in the following Example.

EXAMPLE 20

3-Carboxy-23-methyl-21-nor-3,5-choladien-20-one

Step E (Route 3)

Saponification of the product of Example 19 gave, after acidification and recrystallization from acetonitrile, the title compound, m.p. 221°–223° C., λ max: 263 nm ($\epsilon$=14,200).

Anal. Calcd. for $C_{25}H_{36}O_3 \cdot 0.2 H_2O$ C, 77.35; H, 9.45. Found: C, 77.47; H, 9.46.

EXAMPLE 21

3-Carbomethoxy-3,5-androstadiene-17β-carboxylic acid

Step D (Route 2)

A solution of the product of Example 1 (3.0 g., 6.7 mmoles) in 100 ml. of 1:1 methanol/DMF was reacted with carbon monoxide in the presence of 1.35 g. of triethylamine, 156 mg. of triphenylphosphine and 60 mg. of palladium acetate. The reaction was carried out in a fashion analogously to that of Example 4 with chloroform as the workup solvent. Chromatography on silica gel eluted with 2:1 hexane/ethyl ether containing 0.5% formic acid afforded 700 mg of the title compound which was identified by its nmr and mass spectra. The corresponding diacid and diester were also isolated.

EXAMPLE 22

S-(2-Pyridyl) 3-carbomethoxy-3,5androstadiene-17β-thiocarboxylate

Step B (Route 2)

Using an analogous procedure to Example 2, the product of Example 21 was converted to the title compound which was characterized by its nmr and mass spectra.

EXAMPLE 23

Methyl 17β-[4'-(tert-butyldimethylsiloxy)benzoyl]-3,5-androstadien-3-carboxylate

Step C (Route 2)

Reaction of the product of the previous Example with 4-tert-butyldimethylsiloxyphenyl magnesium bromide by the procedure described in Example 3 gave analogously, after a chromatographic workup, the title compound as a non-crystalline solid. This material had an nmr spectrum identical to the product of Example 4.

EXAMPLE 24

N-(2-adamantyl)-3-oxo-4-androstene-17β-carboxamide

Step C (Route 3)

A solution of 1.49 g. (8 mmoles) of 2-adamantamine hydrochloride in methanol was neutralized with 3.68 ml. of 2.17M sodium methoxide in methanol. The solvent was removed under reduced pressure and the residue was dissolved in 15 ml. anhydrous tetrahydrofuran. To this solution was added the thiopyridyl steroid from Example 8 (423 mg., 1.0 mmole) with stirring. The resulting solution was stirred for 16 hour at 24° C. The solvent was evaporated and the residue, dissolved in methylene chloride, was washed successively with dilute hydrochloric acid, water, 0.5N sodium hydroxide solution and water. The residue obtained on evaporation was dissolved in 20 ml. of methanol containing 1.0 ml. of 2N hydrochloric acid. After standing for 16 hours the solution was concentrated. The residue in methylene chloride was washed with aqueous sodium bicarbonate solution and water. Drying followed by concentration left 500 mg. of a non-crystalline solid. Crystallization from acetonitrile gave the title compound, 330 mg., m.p. 244°–246° C.

Anal. Calcd: C, 80.13; H, 9.64; N, 3.12. Found: C, 79.83; H, 9.62; N, 3.22.

EXAMPLE 25

N-(2-Adamantyl)3-(trifluoromethanesulfonyloxy)-3,5-androstadiene-17β-carboxamide

Step A (Route 3)

A solution of the adamantyl amide from Example 24 (350 mg., 0.73 mmole), 2,6di-tert-butyl-4-methylpyridine (211 mg., 1.03 mmole) and trifluoromethane sulfonic anhydride (416 mg., 1.48 mmole) in 5 ml. of methylene chloride was prepared at 0° C. The mixture warmed to room temperature and was kept at 24° C. for 2.5 hours. Additional methylene chloride was added and the solution was washed successively with dilute hydrochloric acid, dilute sodium bicarbonate solution and water. The residue obtained on concentration was eluted on 3–2000μ silica gel plates with 5% acetone in methylene chloride. Starting material and the title compound were isolated. The latter, 376 mg., was identified by its nmr and mass spectra.

EXAMPLE 26

N-(2-Adamantyl)-3-carbomethoxy-3,5-androstadiene-17β-carboxamide

Step D (Route 3)

Into a solution prepared from 350 mg. (0.623 mmole) of the product of the previous Example, 13.5 mg. (0.024 mmole) of triphenylphosphine, 5.4 mg. (0.048 mmole) of palladium diacetate and 126 mg. of triethylamine in a 1:1 mixture of methanol and dimethylformamide was bubbled carbon monoxide at 24° C. The solution was kept under a carbon monoxide atmosphere for 2.5 days. Ethyl acetate was added to the solution followed by water. The layers were mixed and then separated. The organic layer was dried and evaporated. The residue was eluted on 4–1000μ silica plates with 2% acetone in methylene chloride. The major product, 230 mg., was identified as the title compound by its nmr and mass spectra.

EXAMPLE 27

N-(2-Adamantyl)3-carboxy-3,5-androstadien-17β-carboxamide

Step E (Route 3)

A solution of 120 mg. (0.24 mmole) of the product of the previous Example in 25 ml. of a 10% solution of potassium hydroxide in methanol was heated at reflux for 1.0 hour. The solvent was evaporated and the residue was acidified with dilute hydrochloric acid. The ethyl acetate extract was washed with water, dried and evaporated. The residue was crystallized from acetonitrile to leave 60 mg. of the title compound, m.p. 214°–216° C., λ max: 268 (ε=31,800).

Analysis Calcd. for $C_{31}H_{43}NO_3 \cdot 0.5\ H_2O$. C, 76.50; H, 9.11; N, 2.88. Found: C, 76.58; H, 9.35; N, 2.96.

What is claimed is:

1. A compound of the formula:

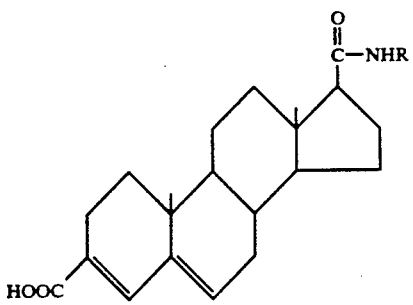

wherein R is a hydrocarbon radical selected from 1-or 2-adamantyl, 1-, 2- or 7-norbornanyl, and pharmaceutically acceptable salts or esters thereof, said adamantyl and said nonbornanyl being optionally substituted with a member selected from the group consisting of $C_1$–$C_4$ straight chain or branched alkyl, nitro, oxo, $C_7$–$C_9$ aralkyl, $(CH_2)_n\ COOR^1$ where n is 0–2 and $R^1$ is H; straight chain or branched $C_1$–$C_4$ alkyl, $CH_2OH$, OH, $OR^2$ where $R^2$ is $C_1$–$C_4$ straight chain or branched alkyl, halo, $CONH_2$, $CH_2NH_2$, $CH_2NHCOR^3$ where $R^3$ is $C_1$–$C_4$ straight chain or branched alkyl; phenyl; or, p-substituted phenyl wherein the substituents are members selected from the group consisting of nitro, amino, sulfo or cyano.

2. The compound of claim 1 wherein the compound is 17β(N-2-adamantylcarbamoyl)-3-carboxy-androst-3,5-diene.

3. The compound of claim 1 wherein the compound is 17β(N-1-adamantylcarbamoyl)-3-carboxy-androst-3,5-diene.

4. A method of treating the hyperandrogenic condition of acne vulgaris, seborrhea, female hirsutism, and benign prostatic hypertrophy comprising parenteral administration to a patient in need of such treatment of a therapeutically effective amount of a compound of claim 1.

5. A pharmaceutical composition comprising a pharmaceutically acceptable carrier and a therapeutically effective amount of a compound according to claim 1.

* * * * *